United States Patent [19]

Heindl et al.

[11] Patent Number: 5,352,701
[45] Date of Patent: Oct. 4, 1994

[54] LEUKOTRIENE-B₄ ANTAGONIST COMPOUNDS AND THEIR USE AS PHARMACEUTICAL AGENTS

[75] Inventors: Josef Heindl; Werner Skuballa; Bernd Buchmann; Wolfgang Frohlich; Roland Ekerdt; Claudia Giesen, all of Berlin, Fed. Rep. of Germany

[73] Assignee: Schering Aktiengesellschaft, Berlin und Bergkamen, Fed. Rep. of Germany

[21] Appl. No.: 50,195

[22] Filed: May 5, 1993

[30] Foreign Application Priority Data

Sep. 7, 1990 [DE] Fed. Rep. of Germany ....... 4028866

[51] Int. Cl.⁵ .................. C07C 65/40; A61K 31/19
[52] U.S. Cl. ...................... 514/568; 514/546; 514/617; 560/60; 560/61; 562/471; 562/493; 564/182
[58] Field of Search ............. 560/61, 60; 564/182; 562/471, 493; 514/546, 568, 617

[56] References Cited

U.S. PATENT DOCUMENTS

4,992,576  2/1991  Gapinski ..................... 560/52

FOREIGN PATENT DOCUMENTS

276064  7/1988  European Pat. Off. ............ 560/52

*Primary Examiner*—C. Warren Ivy
*Assistant Examiner*—Zinna N. Davis

[57] ABSTRACT

1. Leukotriene-B₄ antagonists of formula I

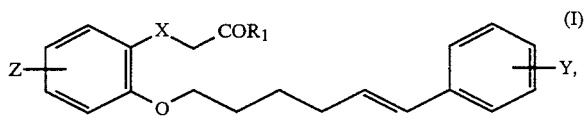

are described, in which
X is a CH₂ group or an oxygen atom,
Y is C₁-C₄-alkoxy or —S(O)$_p$—C₁-C₄-alkyl,
p is 0, 1 or 2
Z is a hydrogen atom or the radical A-B-COOH with A being a hydroxymethylene group or a carbonyl group and B being an alkylene group with 1-6 atoms in the chain or a radical

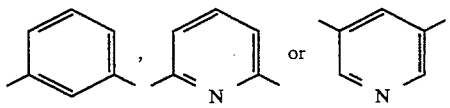

with the exception that B cannot mean the radical

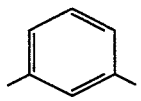

if X is a CH₂ group, R₁ is the radical OH, —O—(C₁—C₄)-alkyl, —O—(C₃-$_{C6}$)-cycloalkyl, —O—(C₇-$_{C12}$)-aralkyl or the radical NHR₄ with R₄ being hydrogen, (C₁-C₄)-alkyl, (C₃-C₆)-cycloalkyl, C₆-C₁₀-aryl or (C₇-C₁₂)-aralkyl as well as their salts with physiologically compatible bases and their cyclodextrin clathrates, process for their production and their use as pharmaceutical agents.

6 Claims, No Drawings

LEUKOTRIENE-B₄ ANTAGONIST COMPOUNDS AND THEIR USE AS PHARMACEUTICAL AGENTS

The invention relates to new leukotriene-B$_4$ antagonists, process for their production as well as their use as pharmaceutical agents.

Leukotriene B$_4$ (LTB$_4$) was discovered in 1979 by B. Samuelsson et al. as a metabolite of arachidonic acid. In the biosynthesis, leukotriene A$_4$ is formed by the enzyme 5-lipoxygenase first as a central intermediate product, which then is converted by a specific hydrolase to the LTB$_4$.

KEY:
Arachidonsäure = arachidonic acid
Leukotrien A$_4$ (LTA$_4$) = leukotriene A$_4$ (LTA$_4$)
Glutathion—S-transferase = glutathione—S-transferase
Leukotrien B$_4$ (LTB$_4$) = leukotriene B$_4$ (LTB$_4$)
Leukotrien C$_4$ (LTC$_4$) = leukotriene C$_4$ (LTC$_4$)

the Future 12, 453 (1987). c) B. Samuelsson et al., Science 237, 1171 (1987). d) C. W. Parker, Drug Development Research 10, 277 (1987). It follows from the above that LTB$_4$ is an important inflammation mediator for inflammatory diseases, in which leukocytes invade the affected tissue.

It is known from the LTB$_4$ that it causes the adhesion of leukocytes on the blood vessel wall. LTB$_4$ is chemotactically active, i.e., it triggers a directionally controlled migration of leukocytes in the direction of a gradient of increasing concentration. Further, because of its chemotactic activity, it indirectly changes the vascular permeability, and a synergism with prostaglandin E$_2$ is observed. LTB$_4$ obviously plays a decisive role in inflammatory, allergic and immunological processes.

Leukotrienes and especially LTB$_4$ are involved in skin diseases, which accompany inflammatory processes (increased vessel permeability and formation of edemas, cell infiltration), increased proliferation of skin cells and itching, such as, for example, in eczemas, erythemas, psoriasis, pruritus and acne. Pathologically

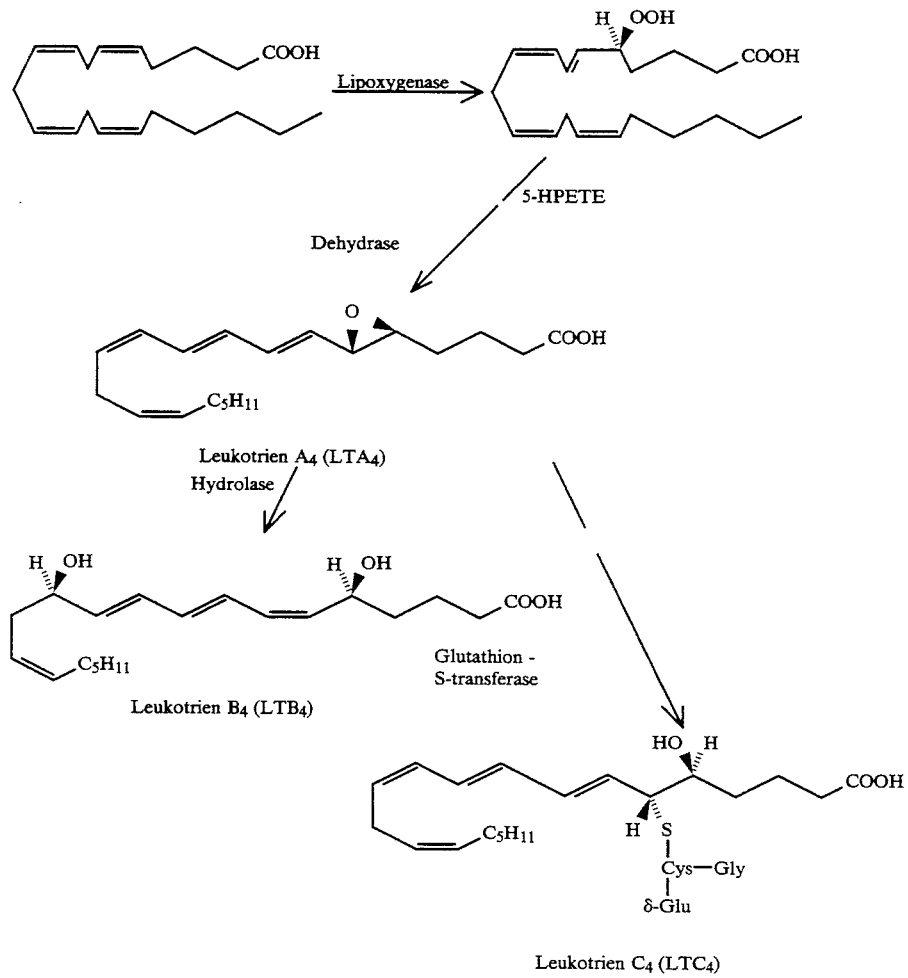

Leukotrien C$_4$ (LTC$_4$)

The nomenclature of the leukotrienes can be gathered from the following papers: a) B. Samuelsson et al., Prostaglandins 19, 645 (1980); 17,785 (1979). b) C. N. Serhan et al., Prostaglandins 34, 201 (1987).

The physiological and especially the pathophysiological importance of leukotriene B$_4$ is summarized in several more recent papers: a) The Leukotrienes, Chemistry and Biology eds. L. W. Chakrin, D. M. Bailey, Academic Press 1984. b) J. W. Gillard et al., Drugs of increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis.

Further, leukotrienes and LTB$_4$ are involved especially in arthritis, chronic lung diseases (e.g., asthma), rhinitis and inflammatory intestinal diseases.

Antagonists against LTB$_4$ itself or inhibitors of those enzymes which are involved in the synthesis of the LTB$_4$, can be effective as specific medications, especially against diseases which accompany inflammations and allergic reactions.

From EP276064 compounds with a carboxybenzene-phenylpropionic acid structure, that have leukotriene-D$_4$ and leukotriene-B$_4$ antagonistic properties, are already known.

Compounds were found that are surprisingly strongly antagonistic to the effect of natural LTB$_4$.

The invention relates to leukotriene-B$_4$ antagonists of formula I

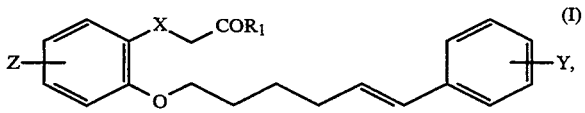

in which

X means a CH$_2$ group or an oxygen atom,

Y means C$_1$-C$_4$-alkoxy or —S(O)$_p$—C$_1$-C$_4$-alkyl, p means 0, 1 or 2

Z means a hydrogen atom or the radical A-B-COOH with A meaning a hydroxymethylene group or a carbonyl group and B meaning an alkylene group with 1-6 atoms in the chain or a radical

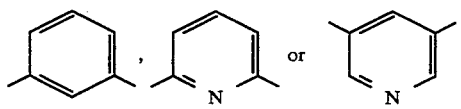

with the exception that B does not mean the radical

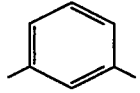

if X represents a CH$_2$ group, R$_1$ represents the radical OH, —O—(C$_1$-C$_4$)-alkyl, —O—(C$_3$-C$_6$)-cycloalkyl, —O—(C$_6$-C$_{10}$)-aryl, —O—(C$_7$-C$_{12}$)—aralkyl or the radical NR$_4$R$_6$ with R$_4$ meaning hydrogen, (C$_1$-C$_4$)-(C$_3$-C$_6$)-cycloalkyl or (C$_7$-C$_{12}$)-aralkyl and R$_6$ meaning (C$_1$-C$_4$)-alkyl, (C$_3$-C$_6$)-cycloalkyl or (C$_7$-C$_{12}$)-aralkyl as well as their salts with physiologically compatible bases and their cyclodextrin clathrates.

Y and R$_1$ as the C$_1$-C$_4$-alkoxy group can mean: methoxy, ethoxy, n-propoxy, isoproxy, n-butoxy, sec.-butoxy and tert.-butoxy.

The C$_1$-C$_4$-alkyl radical in the group —S(O)$_p$=(-C$_1$-C$_4$)-alkyl of Y or as radical R or R$_4$ can be: methyl, ethyl, n-propyl-isopropyl, n-butyl, sec.-butyl, tert.-butyl.

As alkylene group Z with 1-6 C atoms straight-chain or branched-chain, saturated radicals are suitable, such as, e.g., methylene, ethylene, trimethylene, tetramethylene, hexamethylene, 1-methyltrimethylene, 1-methyltetramethylene, 1,1-diemthyltrimethylene etc.

The radical (C$_3$-C$_6$)-cycloalkyl (for R$_1$ and R$_4$) can be: cyclopropyl, cyclobutyl, cyclopentyl or cyclohexyl.

As radicals C$_6$-C$_{10}$-aryl in the definition of R$_1$, phenyl, 1-naphthyl, 2-naphthyl are suitable.

Finally radicals C$_7$-C$_{12}$-aralkyl in the definitions of R$_1$ and R$_4$ represent the following groups: benzyl, phenethyl, 3-phenylpropyl, 4-phenylbutyl, 1-methyl-3-phenylpropyl, 1-methyl-2-phenyl-ethyl, etc.

Inorganic and organic bases as they are known to one skilled in the art for forming physiologically compatible salts are suitable for salt formation. For example, there can be mentioned alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morphine, tris-(hydroxymethyl)-methylamine, etc.

The compounds of formula I are reacted with α, β or γ-cyclodextrin to achieve the cyclodextrin clathrates. Preferred are the β-cyclodextrin clathrates.

The invention further relates to a process for the production of the leukotriene-B$_4$ antagonists of formula I, characterized in that, in a way known in the art, a compound of formula II

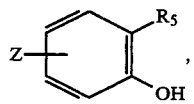

in which Z has the above-indicated meaning and R$_5$ means radicals OH or X—CH$_2$—COOR, and X has the above-indicated meaning and R represents a C$_1$-C$_4$-alkyl group, is reacted with a compound of formula III

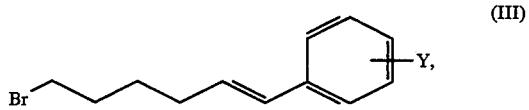

in which Y has the above-indicated meaning, in the presence of cesium carbonate, lithium carbonate or potassium carbonate and in case R$_5$ means the radical OH is reacted with a compound of formula IV BrCH$_2$COOR (IV), in which R has the above-indicated meaning, carbonyl group A is optionally reduced, ester groups are saponified, carboxyl groups are esterified or the resulting acids of formula I are reacted with organic or inorganic bases or cyclodextrins.

The above-mentioned process (II+III—I) is performed in organic solvents, such as, e.g., dimethylformamide, at temperatures between 0° and 100° C., preferably at temperatures between 20° and 60° C. with stirring in the course of 5-24 hours in the presence of cesium carbonate, lithium carbonate or potassium carbonate.

The reduction of carbonyl group A preferably takes place with sodium borohydride under the usual conditions. The resulting hydroxymethylene compounds optionally can be separated in the optical antipodes.

The production of the compounds of formula II and III necessary for this reaction takes place according to the processes indicated in the examples or in the reference examples.

The saponification of the esters of formula I is performed according to the methods known to one skilled in the art, such as, for example, with basic catalysts. The introduction of the ester group

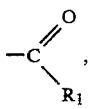

in which $R_1$ represents an O-alkyl group with 1–4 C atoms, takes place according to methods known to one skilled in the art. The 1-carboxy compounds are reacted, for example, with diazohydrocarbons in a way known in the art. The esterification with diazohydrocarbons takes place, e.g., in that a solution of diazohydrocarbon is mixed in an inert solvent, preferably in diethylether, with the 1-carboxy compound in the same or in another inert solvent, such as, e.g., methylene chloride. After completion of the reaction in 1 to 30 minutes the solvent is removed and the ester is purified in the usual way. Diazoalkanes are either known or can be produced according to known methods [Org. Reactions Vol. 8, pages 389–394 (1954)].

The introduction of the ester group

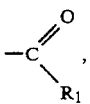

in which $R^1$ represents an —O—aryl group, takes place according to methods known to one skilled in the art. For example, the 1-carboxy compounds are reacted with the corresponding arylhydroxy compounds with dicyclohexylcarbodiimide in the presence of a suitable base, for example, pyridine, DMAP, triethylamine, in an inert solvent. As solvent, methylene chloride, ethylene chloride, chloroform, ethyl acetate, tetrahydrofuran, preferably chloroform, are suitable. The reaction is performed at temperatures between −30° C. and +50° C., preferably at 10° C.

The leukotriene-$B_4$ antagonists of formula I with $R_1$ meaning a COOH group can be converted to a salt with suitable amounts of the corresponding inorganic bases with neutralization. For example, during dissolving of the corresponding acids in water, which contains the stoichiometric amount of the base, the solid inorganic salt is obtained after evaporation of the water or after addition of a water-miscible solvent, e.g., alcohol or acetone.

For the production of an amine salt, the $LTB_4$ acid, e.g., is dissolved in a suitable solvent, for example, ethanol, acetone, diethyl ether, acetonitrile or benzene and at least the stoichiometric amount of the amine is added to this solution. In this way, the salt usually accumulates in solid form or is isolated after evaporation of the solvent in the usual way.

The introduction of the amide group

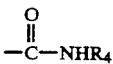

takes place according to methods known to one skilled in the art. The carboxylic acids of formula I ($R_1$=OH) are first converted in the presence of a tertiary amine, such as, for example, triethylamine, with chloroformic acid isobutylester into the mixed anhydride. The reaction of the mixed anhydrides with the alkali salt of the corresponding amine or with ammonia takes place in an inert solvent or solvent mixture, such as, for example, tetrahydrofuran, dimethoxyethane, dimethylformamide, hexamethylphosphoric acid triamide at temperatures between −30° C. and +60° C., preferably at 0° C. to 30° C.

The compounds of formula I act in an antiinflammatory and antiallergic manner. Consequently, the new leukotriene-$B_4$ derivatives of formula I represent valuable pharmaceutical active ingredients. The compounds of formula I are especially suitable for topical administration, since they exhibit a dissociation between desired topical effectiveness and undesirable systemic side effects.

The new leukotriene-$B_4$ antagonists of formula I are suitable in combination with the auxiliary agents and vehicles usual in galenic pharmaceutics for topical treatment of contact dermatitis, eczemas of the most varied types, neurodermatoses, erythrodermia, pruritus vulvae et ani, rosacea, cutaneus lupus erythematosus, psoriasis, lichen ruber planus et verrucosis and similar skin diseases.

The production of the pharmaceutical agent specialties takes place in the usual way, by the active ingredients being converted with suitable additives to the desired form of administration, such as, for example: solutions, lotions, ointments, creams or plasters.

In the thus formulated pharmaceutical agents, the active ingredient concentration depends on the form of administration. In lotions and ointments, an active ingredient concentration of 0.0001% to 1% is preferably used.

Further, the new compounds optionally in combination with the usual auxiliary agents and vehicles are also well-suited for the production of inhalants, which can be used to treat allergic diseases of the respiratory system, such as, for example, bronchial asthma or rhinitis.

The new leukotriene-$B_4$ antagonists are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat allergic diseases of the intestinal tract, such as colitis ulcerosa and colitis granulomatosa.

The new leukotriene-$B_4$ derivatives can also be used in combination with, e.g., lipoxygenase inhibitors, cyclooxygenase inhibitors, prostacyclin agonists, prostaglandin agonists, thromboxane antagonists, leukotriene-$D_4$ antagonists, leukotriene-granulomatosa. $E_4$ antagonists, leukotriene-$F_4$ antagonists, phosphodiesterase inhibitors, calcium antagonists or PAF antagonists.

REFERENCE EXAMPLES 1) (5E,Z) -6-(4-Methoxyphenyl) -5-hexenoic acid methyl ester A total of 49.6g of potassium-tert.-butylate is added in portions under argon at 0° C. to 97.7g of carboxybutyl-triphenylphosphonium bromide in 205 ml of dimethyl-sulfoxide/108 ml of tetrahydrofuran and stirred for 1 hour at 0° C. Then 11.2g of 4-methoxybenzaldehyde dissolved in 200 ml of tetrahydrofuran is instilled and stirred for 2.5 hours at 50° C. Then 62.7g of methyliodide dissolved in 50 ml of tetrahydrofuran is instilled and stirred for 16 hours at 24° C. The reaction mixture is poured on 800 ml of ice water, extracted three times each with 400 ml of methylene chloride, dried on sodium sulfate and concentrated by evaporation in a vacuum. The residue is purified by flash chromatography on silica gel with hexane/10–20% ethyl acetate. 15.8g of the title compound is obtained as colorless oil.

IR: 3005, 2958, 2842, 1730, 1608, 1510, 1440, 1248, 1175, 1033, 968, 842 cm$^{-1}$.

2) (5E)-6-(4-Methoxyphenyl)-5-hexen-1-ol 139 ml (168mmol) of a DIBAH solution in toluene is instilled under argon at −70° C. in 15.7g of the above produced ester in 490 ml of toluene and allowed to heat for 2 hours to −10° C. Then 56 ml of isopropanol followed by 80 ml of water are carefully added at −70° C. and stirred for 2 hours at 24° C. It is filtered off from the precipitate and washed well with ethyl acetate. The thus obtained residue is dissolved in 800 ml of dimethyl-sulfoxide/tetrahydrofuran (1+1), mixed with 24g of potassium-tert.-butylate under argon at 24° C. and stirred for 15 hours at 24° C. Then it is poured on 1000 ml of ice water, extracted five times with ether, the combined organic phases are washed with brine, dried on magnesium sulfate and concentrated by evaporation in a vacuum. The residue is purified by flash chromatography on silica gel with hexane/20–50% ethyl acetate. A prepurified product is obtained which is purified again by recrystallization from hexane/toluene. 9.6g of the title compound is obtained as colorless crystals. Melting point 66° C.

IR: 3625, 3460, 3008, 2940, 2842, 1610, 1512, 1245, 1176, 1037, 968 cm$^{-1}$.

3) (1E)-6-Bromo-1-(4-methoxyphenyl)-1-hexene 2 ml of pyridine, 6.62g of tetrabromomethane and 5.0g of triphenylphosphine are added at −78° C. under argon to a solution of 4.18g of the above produced alcohol in 200 ml of methylene chloride. It is allowed to heat with stirring for 1.5 hours to 24° C. It is concentrated by evaporation in a vacuum and the residue is chromatographed on silica gel with hexane/10–20% ethyl acetate. 5.2g of the title compound is obtained as colorless oil.

IR: 3000, 2970, 2938, 1610, 1512, 1438, 1247, 1105, 968 cm$^{-1}$.

EXAMPLE 1

3-[2-[6-(4-Methoxyphenyl)-(5E)-5-hexenyloxy]-phenyl]-propionic acid

A. 651 mg of cesium carbonate is added to a solution of 180 mg of 3-(2-hydroxyphenyl)-propionic acid methyl ester and 272 mg of (1E)-6-bromo-1-(4-methoxyphenyl)-1-hexene in 2 ml of dimethylformamide and the suspension is stirred for 16 hours at room temperature. The reaction mixture is filtered, the filtration residue is washed with dichloromethane, the filtrate concentrated by evaporation and the residue chromatographed on silica gel with hexane. 255 mg of 3-[2-[6-(4-methoxyphenyl)(5E)-5-hexenyloxy]-phenyl]-propionic acid methyl ester is obtained as oil.

IR: (CHCl$_3$): 2942, 1730, 1610, 1512, 1498, 1241, 1110, 1030, 969 cm$^{-1}$.

B. A solution of 100 mg of 3-[2-[6-(4-methoxyphenyl)-(5E)5-hexenyloxy]-phenyl]-propionic acid methyl ester in 2 ml of methanol and 2 ml of in potassium hydroxide solution is stirred for 2 ½ hours at room temperature. The reaction mixture is acidified to pH 1 with 2 n hydrochloric acid and shaken out with ethyl acetate, the organic phase is dried on sodium sulfate and concentrated by evaporation. 92 mg of the title compound is obtained as oil.

IR: (CHCl$_3$): 2940, 1710, 1608, 1510, 1498, 1245, 1100, 1015, 968 cm$^{-1}$.

EXAMPLE 2

5-(3-Carboxybenzoyl)-2-[6-(4-methoxyphenyl)-(5E)-5-hexenyloxy]-phenoxy-acetic acid A. 14.8g of aluminum chloride and 5g of veratrole are added to a solution of 7.34g of isophthalic acid monomethyl ester chloride in 160 ml of dichloromethane under ice cooling. The reaction mixture is refluxed for 8 hours, poured on ice water, acidified with 2 n of hydrochloric acid and shaken out with dichloromethane. The organic phase is dried on sodium sulfate, concentrated by evaporation and the residue is chromatographed on silica gel with hexane/ethyl acetate=8/2. 3.5g of 3-(4-hydroxy-3-methoxybenzoyl)-benzoic acid methyl ester of melting point of 133°–134° C. is obtained.

IR: (CHCl$_3$): 3520, 2945, 1715, 1644, 1590, 1500, 1423, 1310, 1265 cm$^{-1}$.

B. 3.4g of 3-(4-hydroxy-3-methoxybenzoyl)-benzoic acid methyl ester is mixed with 43g of pyridine-hydrochloride and heated with stirring to 180° C. for 4 hours. After cooling to 90° C., the reaction mixture is mixed with water, shaken out with dichloromethane, dried on sodium sulfate and concentrated by evaporation. 2.9g of 3-(3,4-dihydroxy-benzoyl)-3-(3,4-dihydroxy-benzoyl)-benzoic acid of melting point of 254°–256° C. is obtained.

IR (KBr): 3510, 3300, 1740, 1700, 1640, 1590, 1579, 1440, 1318, 1240, 1120, 740, 715, 615 cm$^{-1}$.

C. A solution of 2.9g of 3-(3,4-dihydroxybenzoyl)-benzoic acid in 100 ml of methanol is mixed with 7g of Amberlyst 15 ® and refluxed with stirring for 8 hours. The reaction mixture is filtered on diatomaceous earth, the filtrate concentrated by evaporation, taken up in ethyl acetate and shaken out with 10% sodium bicarbonate solution. The organic phase is dried on sodium sulfate and concentrated by evaporation. 1.4g of 3-(3,4-dihydroxybenzoyl)-benzoic acid methyl ester is obtained as oily crude product. 272 mg of this crude product is dissolved in 2.5 ml of dimethylformamide, mixed with 269 mg of (1E)-6-bromo-1-(4-methoxyphenyl)-1-hexene and 185 mg of lithium carbonate and the mixture is heated for 18 hours to 50°–60° C. with stirring. The reaction mixture is filtered, washed with dichloromethane, the filtrate is concentrated by evaporation and the residue is chromatographed on silica gel with hexane/ethyl acetate=98/2. 230 mg of 3-[3-hydroxy-4-[6-(4-methoxyphenyl)-(5E)-5-hexenyloxy]benzoyl]-benzoic acid methyl ester is obtained as oil.

IR: (CHCl$_3$): 3670, 3535-3330, 2995, 2935, 1723, 1670, 1610, 1500, 1386, 1255, 1091, 970 cm$^{-1}$.

D. Under the conditions of example 1A, 240 mg of 3-[3-hydroxy-4-[6-4-methylphenyl)-(5E)-acid methyl ester is reacted with 87 mg of bromoacetic acid ethyl ester, worked up and chromatographed on silica gel with hexane/ethyl acetate =8/2. 120 mg of 5-(3-methoxycarbonyl-benzoyl)-2-[6-(4-methoxyphenyl)-(5E)-5-hexenyloxy]-phenoxy acetic acid ethyl ester is obtained as colorless oil.

IR (Film): 2950, 2840, 1758, 1725, 1653, 1598, 1512, 1430, 1309, 1250, 1138, 1034, 968, 741, 724 cm$^{-1}$.

E. Under the conditions of example 1B, 30 mg of 5-(3-methoxycarbonylbenzoyl)-2-[6-(4-methoxyphenyl)-(5E)-5-hexenyloxy]-phenoxy acetic acid ethyl ester is saponified in 1 ml of methanol with 1 ml of In sodium hydroxide solution and worked up. 22 mg of 5-(3-carboxybenzoyl)-2-[6-(4-methoxyphenyl)-(5E)-

5hexenyloxy]-phenoxy acetic acid is obtained as colorless oil.

IR: (CHCl$_3$): 2960, 1728, 1603, 1510, 1260, 1095, 1011 cm$^{-1}$.

EXAMPLE 3

5-[3-(2-Carboxyethyl)-4-[6-(4-methoxyphenyl)-(5E)-5hexenyloxy]-phenyl]-5-oxopentanoic acid A. 5.1g of glutaric acid monomethyl ester chloride and 5g of 3-(2-methoxyphenyl)-propionic acid methyl ester are added with ice cooling in succession to a suspension of 10g of aluminum chloride in 100 ml of dichloromethane and the mixture is stirred for 16 hours at room temperature. The reaction mixture is poured on ice/2n hydrochloric acid, shaken out with dichloromethane, the organic phase is dried on sodium sulfate and concentrated by evaporation. The residue is chromatographed on silica gel with hexane/ethyl acetate (0–30% ethyl acetate). 4.45g of 5-[4-methoxy-3-(2-methoxycarbonylethyl)-phenyl]-5-oxo-pentanoic acid methyl ester is obtained as oil, that is heated together with 47.5g of pyridinehydrochloride for 5 hours to 180° C. for further reaction. After cooling to 90° C. the reaction mixture is mixed with water, acidified to pH 1 with concentrated hydrochloric acid, shaken out with ethyl acetate, the organic phase is dried on sodium sulfate and concentrated by evaporation. 3.9g of 5[3-(2-carboxyethyl)-4-hydroxyphenyl]-5-oxopentanoic acid of melting point of 169°–166° C. is obtained.

IR (KBr): 3370, 1700, 1660, 1590, 1282, 1154, 1118 cm$^{-1}$.

B. A solution of 3.7g of 5-[3-(2-carboxyethyl)-4hydroxyphenyl]-5-oxopentanoic acid in 190 ml of methanol is mixed with 7.7g of Amberlyst 15 ® and stirred for 24 hours at room temperature. The reaction mixture is filtered on diatomaceous earth, the filtrate concentrated by evaporation, taken up in ethyl acetate and shaken out with 10% sodium bicarbonate solution. The organic phase is dried on sodium sulfate, concentrated by evaporation and the residue is chromatographed on silica gel with hexane/ethyl acetate (5–35% ethyl acetate). 3.38g of 5-[4-hydroxy-3-(2-methoxycarbonylethyl)-phenyl]-5-oxopentanoic acid methyl ester is obtained as oil.

IR (Film): 3700–3040, 2950, 1730, 1715, 1670, 1595, 1505, 1435, 1360, 1280, 1163, 1118, 1015 cm$^{-1}$.

C. Under the conditions of example 1A, 500 mg of 5-[4-hydroxy-3-(2-methoxycarbonylethyl)-Phenyl]-5-oxo-pentanoic acid methyl ester is reacted with 436 mg of (1E)-6-bromo-1-(4-methoxyphenyl)-1-hexene, worked up and the crude product is chromatographed on silica gel with hexane/ethyl acetate (0–15% ethyl acetate). 657 mg of 5-[3-(2-methoxycarbonylethyl)-4-[6-(4-methoxyphenyl)-( 5E)-5-hexenyloxy]-phenyl]-5-oxopentanoic acid methyl ester is obtained as oil.

IR (CHCl$_3$): 2955, 1732, 1675, 1602, 1510, 1440, 1248, 1185, 1120, 1034, 968 cm$^{-1}$.

D. A solution of 400 mg of 5-[3-(2-methoxycarbonylethyl)-4-[6-(4-methoxyphenyl)-(5E)-5-hexenyloxy]-phenyl]-5-oxo-pentanoic acid methyl ester in 33 ml of methanol and 13 ml of in sodium hydroxide solution is stirred for 16 hours at room temperature. The methanol is distilled off in a vacuum, the alkaline solution is acidified with in hydrochloric acid to pH 1, shaken out with ethyl acetate, the organic phase is dried on sodium sulfate and concentrated by evaporation. 272 mg of the title compound of the melting point of 113°–114° is obtained.

IR (CHCl$_3$): 3685, 3600–3140, 2940, 1713, 1680, 1607, 1512, 1250, 1180, 970 cm$^{-1}$.

EXAMPLE 4

3-{5-[6-Carboxy-2,pyridylcarbonyl]-2-[6-(4-methoxyphenyl)-(5E)-5-hexenyloxy]-phenyl}-propionic acid A. 2.2g of 6-methoxycarbonyl-pyridine-2-carboxylic acid chloride and 1.0g of 3-(2-methoxyphenyl)-propionic acid methyl ester are added in succession to a suspension of 4.4g of aluminum chloride in 50 ml of dichloromethane with ice cooling and the mixture is stirred for 16 hours at room temperature. The reaction mixture is poured on ice/2n hydrochloric acid, shaken out with dichloromethane, the organic phase is dried on sodium sulfate and concentrated by evaporation. The residue is chromatographed on silica gel with hexane/ethyl acetate (0–15%).

1.32g of 3-[5-(6-methoxycarbonyl-2-pyridylcarbonyl)-2methoxyphenyl]-propionic acid methyl ester of melting point 97°–98° C. is obtained.

IR (CHCl$_3$): 2960, 1730, 1655, 1600, 1330, 1260, 1120, 1012 cm$^{-1}$.

B. 1.3g of 3-[5-(6-methoxycarbonyl-2-pyridylcarbonyl)-2-methoxyphenyl]-propionic acid methyl ester is refluxed in 12 ml of 62% hydrobromic acid for 12 hours. The reaction mixture is poured on ice/water, the precipitate is suctioned off and dried. The crude product (1.2g) is refluxed in 11 ml of methanol with 3 drops of concentrated sulfuric acid and concentrated by evaporation. The residue is taken up in ethyl acetate, shaken out with 10% sodium bicarbonate solution, washed with saturated common salt solution, dried on sodium sulfate and concentrated by evaporation. The residue is chromatographed on silica gel with hexane/ethyl acetate (0–40%). 640 mg of 3-[5-(6-methoxycarbonyl-2-pyridylcarbonyl)-2-hydroxyphenyl]-proPionic acid methyl ester of melting point 121°–122° C. is obtained.

IR (CHCl$_3$): 3460–3120, 2945, 1720, 1650, 1598, 1580, 1435, 1225, 1133 cm$^{-1}$.

C. Under the conditions of example 1A, 640 mg of 3-[5-(6-methoxycarbonyl-2-pyridylcarbonyl)-2-hydroxyphenyl]-propionic acid methyl ester is reacted with 505 mg of (1E)-6-bromo-1-(4-methoxyphenyl)- 1-hexene, worked up and the crude product chromatographed on silica gel with hexane/ethyl acetate (0–15%). 732 mg of 3-{5-[6-methoxycarbonyl-2-pyridylcarbonyl]-2-[6-(4-methoxyphenyl)-(5E)-5-hexenyloxy]-phenyl}-propionic acid methyl ester of melting point 80°–82° C. is obtained.

IR (CHCl$_3$): 2940, 1722, 1650, 1595, 1500, 1433, 1325, 1240, 1110 cm$^{-1}$.

D. Under the conditions of example 3D, 65 mg of 3-(5-[6-methoxycarbonyl-2-pyridylcarbonyl]-2-[6-(4-methoxyphenyl)-(5E)-5hexenyloxy]-phenyl}-propionic acid methyl ester in 2 ml of methanol is saponified with 1 ml of sodium hydroxide solution and worked up. 42 mg of the title compound of melting point 163°166° C. is obtained.

IR (KBr): 3700–3320, 3935, 1705, 1655, 1600, 1515, 1265, 1115, 758 cm$^{-1}$.

EXAMPLE 5

3-{5-[6-Carboxy-2-pyridyr(1RS)-1-hydroxymethyl]-2-[6-(4-methoxyphenyl)-(5E)-5-hexenyloxy]-phenyl}-propionic acid A. A solution of 100 mg of 3-{5-[6-methoxycarbonyl-2pyridylcarbonyl]-2-[6-(4-methoxyphenyl)-(5E)-5-hexenyloxy]phenyl}-propionic acid methyl ester in 5 ml of methanol is mixed with 10 mg of sodium borohydride with ice cooling and stirred for 16 hours at room temperature. The reaction mixture is diluted with water, acidified with in sulfuric acid to pH 6, shaken out with ethyl acetate, the organic phase is dried on sodium sulfate and concentrated by evaporation. The residue is chromatographed on silica gel with dichloromethane/methanol (0–2%). 58 mg of 3-[5-$^8$6-methoxycarbonyl-2-pyridyl- (1RS) -1-hydroxymethyl$^9$-2-$^8$6- (4methoxyphenyl)-(5E) -5-hexenyloxy$^9$-phenyl]-propionic acid methyl ester is obtained as colorless oil.

IR (CHCl$_3$): 2925, 2855, 1730, 1610, 1505, 1440, 1248, 1040 cm$^{-1}$.

B. Under the conditions of example 3D, 9 mg of 3-[5-$^8$6-methoxycarbonyl-2-pyridyl-(1RS)-1-hydroxymethyl$^9$-2-$^8$6-(4-methoxyphenyl)-(5E)-5-hexenyloxy$^9$-phenyl]-propionic acid methyl ester in 1 ml of methanol is saponified with 0.5 ml of 2 n sodium hydroxide solution and worked up. 8 mg of the title compound is obtained as colorless oil.

IR (CHCl$_3$): 3700-3140, 2930, 1720, 1610, 1518, 1250, 1120, 620 cm$^{-1}$.

EXAMPLE 6

5-(3-(1-Carboxymethyl)-4-$^8$6-(4-methoxyphenyl)-(5E)-5-hexenyloxy$^9$-phenyl)-5-oxo-pentanoic acid A. Under the conditions of example 3A, 28.8g of aluminum chloride in 320 ml of dichloromethane is reacted with 11.9g of glutaric acid monomethyl ester chloride and 10g of veratrole, worked up and chromatographed. The thus obtained crude product is further reacted under the conditions of example 3A with 270g of pyridinehydrochloride and worked up. 5.6g of 5-(3,4-dihydroxyphenyl)- 5-oxo-pentanoic acid of melting point 210°–215° C. is obtained as crude product.

B. A solution of 5.6g of 5-(3,4-dihydroxyphenyl)-5-oxopentanoic acid in 300 ml of methanol is stirred together with 15g of Amberlyst 15 for 16 hours at room temperature. The reaction mixture is filtered on diatomaceous earth, concentrated by evaporation and the residue is chromatographed on silica gel with hexane/ethyl acetate (20-60%). 3.7 g of 5-(3,4-dihydroxyphenyl)-5-oxo-pentanoic acid methyl ester of melting point 104°–106° C. is obtained.

IR (CHCl$_3$): 3480-3010, 2945, 1728, 1670, 1600, 1438, 1285, 1170 cm$^{-1}$.

C. Under the conditions of example 2C, 1.8g of 5-(3,4-dihydroxyphenyl)-5-oxo-pentanoic acid methyl ester in 19 ml of dimethylformamide is reacted in the presence of 1.4g of lithium carbonate with 2.05g of (1E)-6-bromo-1-(4-methoxyphenyl)-1-hexene, worked up and chromatographed. 470 mg of 5-(3-hydroxy-4[6-(4-methoxyphenyl)-(5E)-5-hexenyloxy]-phenyl)-5-oxo-pentanoic acid methyl ester of melting point 78°–80° C. is obtained.

IR (CHCl$_3$): 3680, 3620, 3020, 2395, 1730, 1510, 1420, 1215, 1040, 925 cm$^{-1}$.

D. Under the conditions of example 1A, 420 mg of 5-(3-hydroxy-4-[6-(4-methoxyphenyl)-(5E)-5-hexenyloxy]-phenyl}-5-oxopentanoic acid methyl ester is reacted with 167 mg of bromoacetic acid ethyl ester in 4 ml of dimethylformamide in the presence of 650 mg of cesium carbonate and worked up. 562 mg of 5-{3-(1-ethoxycarbonylmethoxy)-4-[6-(4-methoxyphenyl)-(5E)-5-hexenyloxy]-phenyl}-5-oxo-pentanoic acid methyl ester is obtained as colorless oil.

IR (CHCl$_3$): 2940, 1752, 1733, 1675, 1600, 1510, 1250, 1200, 1150 cm$^{-1}$.

E. Under the conditions of example 3D, 256 mg of 5-(3-(1-ethoxycarbonylmethoxy)-4-[6-(4-methoxyphenyl)-(5E)-5-hexenyloxy]-phenyl}-5-oxo-pentanoic acid methyl ester in 7 ml of methanol and 1 ml of tetrahydrofuran is saponified with 4.3 ml of 2n sodium hydroxide solution and worked up. 105 mg of the title compound of melting point 128°–130° C. is obtained.

IR (CHCl$_3$): 3700-3000, 2960, 1705, 1680, 1600, 1515, 1430, 1250, 1140 cm$^1$.

EXAMPLE 7

5-[1-(3-Carboxyphenyl)-(1RS)-1-hydroxymethyl]-2-[6-(4-methoxyphenyl)-(5E)-5-hexenyloxy]-phenoxy acetic acid Under the conditions of example 5A, 100 mg of 5-(3-carboxybenzoyl)-2-[6-(4-methoxyphenyl)-(5E)-5-hexenyloxy]-phenoxy acetic acid is reacted with 31 mg of sodium borohydride in 5 ml of dioxane and 0.5 ml of water and worked up (>pH 3-4). 90 mg of the title compound is obtained as colorless oil.

IR (CHCl$_3$): 3560-2980, 2960, 2845, 1710, 1603, 1502, 1245, 1115, 868 cm$^{-1}$.

We claim:

1. A leukotriene-B$_4$ antagonist of formula I

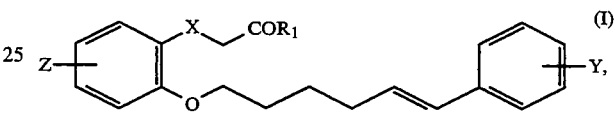

wherein:

X is a CH$_2$ group or an oxygen atom,

Y is C$_1$-C$_4$-alkoxy or —S(O)$_p$—C$_1$-C$_4$-alkyl, p is 0, 1 or 2,

Z is a hydrogen atom or the radical A-B-COOH, with A being a hydroxymethylene group or a carbonyl group and B being an alkylene group with 1-6 atoms in the chain or a radical

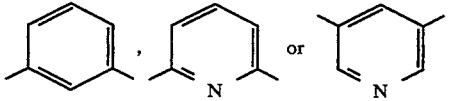

with the exception that B is not the radical

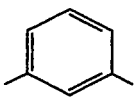

if X is a CH$_2$ group, R$_1$ is the radical OH, —O—(C$_1$-C$_4$)-alkyl, —O—(C$_3$-C$_6$)-cycloalkyl, —O—(C$_6$-C$_{10}$)-aryl, —O—(C$_7$-C$_{12}$)-aralkyl or the radical NHR$_6$, where R$_4$ is hydrogen, (C$_1$-C$_4$)-alkyl, (C$_3$-C$_6$)-cycloalkyl or (C$_7$-C$_{12}$)-aralkyl or salts with physiologically compatible bases and cyclodextrin clathrates thereof.

2. A pharmaceutical agent comprising a compound according to claim 1 and a pharmaceutically acceptable excipient.

3. A compound according to claim 1:
   3-[2-[6-(4-methoxyphenyl)-(5E)-hexenyloxy]-phenyl]-propionic acid.

4. A compound according to claim 1, wherein Y is C$_1$-C$_4$-alkoxy.

5. A compound according to claim 1, wherein Y is CH$_3$—O—.

6. A compound according to claim 1, wherein Y is C$_{1-4}$-alkoxy, X is CH$_2$, and R$_1$ is OH.

* * * * *

UNITED STATES PATENT AND TRADEMARK OFFICE
CERTIFICATE OF CORRECTION

PATENT NO. : 5,352,701
DATED : October 4, 1994
INVENTOR(S) : Josef HEINDL et al.

It is certified that error appears in the above-indentified patent and that said Letters Patent is hereby corrected as shown below:

Claim 1, column 12, lines 33-50: Delete everything appearing after "atom" and before "$R_1$".

Claim 1, column 12, line 53: Change "$R_4$" to --$R_6$--.

Claim 3, column 12, line 60: After "(5E)" insert -- -5- --.

Claim 4, column 12, line 63: Change "$C_1$-$C_4$-alkoxy" to -- $C_{1-4}$-alkoxy --.

Signed and Sealed this

Twenty-fifth Day of July, 1995

Attest:

Attesting Officer

BRUCE LEHMAN

Commissioner of Patents and Trademarks